United States Patent [19]

Mueller

[11] Patent Number: 6,067,988
[45] Date of Patent: May 30, 2000

[54] METHOD FOR CREATION OF DRUG DELIVERY AND/OR STIMULATION POCKETS IN MYOCARDIUM

[75] Inventor: Richard L. Mueller, Sunnyvale, Calif.

[73] Assignee: Eclipse Surgical Technologies, Inc., Sunnyvale, Calif.

[21] Appl. No.: 08/773,778

[22] Filed: Dec. 26, 1996

[51] Int. Cl.$^7$ .................................................. A61B 17/36
[52] U.S. Cl. ................................ 128/898; 606/2; 606/10; 606/15; 606/170; 604/19; 604/20; 604/22
[58] Field of Search ................................. 606/1, 2, 3–19, 606/184–186, 190–194; 604/19, 20, 22; 600/652–662; 128/898

[56] References Cited

U.S. PATENT DOCUMENTS

| 4,846,171 | 7/1989 | Kauphusman et al. . |
| 5,125,926 | 6/1992 | Rudko ....................................... 606/12 |
| 5,133,360 | 7/1992 | Spears ..................................... 600/567 |

FOREIGN PATENT DOCUMENTS

| WO 97/47253 | 12/1997 | WIPO . |
| WO 98/05307 | 2/1998 | WIPO . |

*Primary Examiner*—David M. Shay
*Attorney, Agent, or Firm*—Janet Kaiser Castaneda

[57] ABSTRACT

An apparatus and method for creating drug-filled pockets within muscle tissue, such as myocardium of the heart for increasing angiogenesis. More particularly, the apparatus has an excising assembly with a dilator tip for penetrating and advancing through the surface and body of a muscle or organ, such as the heart. Preferably, the dilator tip has a low level laser optical fiber emission to ease the passage of the excising assembly and provide thermal damage which also stimulates angiogenesis. More preferably, the dilator tip also disperses a pharmacologically active substance as the apparatus is passed through the tissue and/or creates pockets. The excising assembly is connected to a hand-held control device from which the operator pushes a switch to activate a punching mechanism within the excising assembly. The punching mechanism cuts a discrete piece of muscle tissue and traps it within the excising assembly leaving a pocket in the remaining muscle tissue. The excising assembly may also optionally release a bolus of the pharmacologically active substance into the pocket so created. Most preferably, there is a timing mechanism to measure the contraction of the heart, and the timing mechanism is synchronized with the operator's switch on the hand-held device to ensure that the punching occurs at maximum contraction of systole. A measurement guide determines how much excised tissue is trapped in the reservoir of the excising assembly. At a threshold level of filling, the surgeon will remove the excising assembly from the hand-held control device and open the punching mechanism for release of tissue. More preferably, the threshold level of filling will automatically turn off the switch to the punching mechanism to indicate to the surgeon the need to empty the excising assembly of tissue.

44 Claims, 8 Drawing Sheets

METHOD FOR CREATION OF DRUG DELIVERY AND/OR STIMULATION POCKETS IN MYOCARDIUM

FIELD OF INVENTION

This invention relates to the field of microsurgery in creating pocket spaces within muscle tissue, and more particularly to creating intramyocardial pockets for the purposes of drug delivery and/or stimulation of angiogenesis of the myocardium of the heart.

BACKGROUND OF THE INVENTION

Various surgical techniques have been developed to counteract ischemic conditions of the heart, including coronary bypass grafts, angioplasty and for patients who are not suitable candidates for these procedures, or in conjunction with these procedures, transmyocardial revascularization (TMR). In TMR generally, the surgeon creates many narrow channels of approximately one millimeter width that span from an opening at the endocardial surface of a ventricle of the heart, preferably the left ventricle, into the myocardium and then terminating before the epicardial surface. The surgeon generally uses laser to create the channels by either accessing the endocardium through a percutaneous route or the epicardium through an incision into the chest wall. The pressure within the left ventricle at systole forces oxygenated blood into the channels and consequently oxygenates the ischemic myocardium of the left ventricle. Methods of TMR using laser, a combination of laser and mechanical, and solely mechanical apparatus have been disclosed in the prior art, including United States patents such as U.S. Pat. Nos. 4,658,817 (Hardy), 5,125,926 (Rudko, et al) and 5,380,316 and 5,389,096 (Aita, et al) and also more recently in co-pending applications Ser. No. 08/607,782 and Ser. No. 08/713,531.

The percutaneous method does not require the epicardium to be perforated. The surgical method through incision into the chest wall does require perforation of the epicardium to create channels through the myocardium and endocardium which may result in increased peri- and post-operative bleeding. Recent methods described in pending applications Ser. Nos. 08/607,782 abd 08/713,531, however, provide for initial mechanical piercing of the epicardium prior to ablation of myocardial and endocardial tissue by laser which reduces bleeding from the channels into the chest cavity.

A current limit of TMR in revascularizing myocardial tissue includes post-operative closure of a significant proportion of the channels. With little success, attempts have been made by practitioners to maintain the patency of the lumen of the channels through administration of appropriate pharmacologically active compounds. Maintaining a sufficient concentration of such compounds within the channels is very difficult considering the channels are exchanging circulation with the high blood volume interchange of the left ventricle.

TMR's effectiveness in revascularizing ischemic myocardial tissue results not only from the introduction of oxygenated blood into the myocardium through the created channels, but through the increase in angiogenesis in the myocardial tissue surrounding the channels secondary to localized immune-mediated responses. Co-pending application Ser. No. 08/664,956 describes the advantage of creating channels and pockets intramyocardially in stimulating angiogenesis of the myocardium by using laser supplemented optionally with mechanical means. The pockets or channels do not need to be patent at the endocardial surface at creation nor remain patent over time for the angiogenesis stimulation to be effective. The stimulation of angiogenesis occurs through localized immune mediated response to the tissue trauma resulting in an influx of blood borne growth and healing factors and stimulation of capillary growth surrounding the pockets or channels. The oxygenation of myocardial tissue and the functioning capacity of the heart are thereby increased significantly. It is desireable, therefore, to provide an effective concentration of pharmacologically active angiogenic compounds to the myocardium to stimulate angiogenesis on a supplementary or independent basis for the same drug delivery problems as discussed above.

Methods have been disclosed in certain of the above cited art for removing myocardial tissue through laser emission ablation or mechanical cutting techniques to create channels and/or pockets for myocardial revascularization purposes. A noted advantage of using a mechanical cutting tool over the laser method is the ability to cut and remove a discrete piece of tissue. In addition, less bleeding occurs with the use of mechanical as verses laser perforation of the epicardium.

An advantage of using laser over the mechanical method is the reduction in force necessary to pierce the surface and advance through the body of a muscle, and more particularly, piercing the epicardium and advancing through myocardial tissue. The reduction in force allows the surgeon greater ease and control over the procedure. An additional advantage of laser over mechanical surgery is that thermal as compared to mechanical trauma of tissue results in less peri- and post-operative bleeding, less consequential tissue tearing with consequential post-operative fibrous scarring, and potentially greater post-operative immune-mediated reactive angiogenesis.

Methods have been disclosed in certain of the above cited art for synchronizing the laser emission of TMR with the heart beat (as measured by EKG) of the heart (U.S. Pat. No. 5,125,926 (Rudko, et al). These synchronization efforts were made in the attempt to time the emission of the laser with the electrically quiet period of the heart to reduce the occurence of arrhythmias. The peaks of the EKG waves reflect the electrical conductance of the heart, however, and therefore do not directly match the actual contraction of the musculature of the heart. Methods have not been disclosed for synchronizing, directly or indirectly, pocket formation with the contraction of the heart.

The above methods and apparatus and discoveries to date have not provided for concomitant administration of pharmacologically active substances to the channels and/or pockets at their creation. It is therefore desirable to provide an apparatus and method for making distinct pockets within muscle tissue, and in particular, the myocardium, for controllable drug delivery for purposes, among others, of increasing the patency of myocardial channels and/or increasing angiogenesis in the surrounding myocardial tissue. It is further desirable to provide an apparatus and method that simultaneously combines the use of laser and mechanical means to maximize the advantages and minimize the disadvantages of each. Such an apparatus and method is easily controlled by a surgeon, administers moderate thermal damage reducing reactive bleeding and fibrous scarring and increasing reactive immune-mediated localized angiogenesis, cleanly removes all excised tissue, and concomitantly optionally delivers substances or inserts containing pharmacologically active compounds into the formed pocket. It is also further desired to provide an apparatus and method for directly synchronizing the timing of the pocket formation with the contraction of the heart.

SUMMARY OF THE INVENTION WITH OBJECTS

Broadly, an advantage of the present invention is to provide an apparatus and method for creating pockets within muscle tissue for purposes of stimulation and/or delivering substances containing pharmacologically active compounds.

More specifically, an advantage of the present invention is to provide an apparatus and method for creating pockets within the myocardium of the heart, for purposes of stimulation and inserting substances in the pockets that concomitantly are effective in stimulating angiogenesis in surrounding myocardial tissue and/or maintaining the patency of any nearby TMR created channels.

Another advantage of the present invention is to provide an apparatus and method for cleanly removing a distinct piece of tissue from an organ or body tissue through a mechanical punching means thus reducing the likelihood of consequential emboli.

Another advantage of the present invention is to provide an apparatus and method using a reservoir means for storing the excised tissue to allow multiple pockets to be successively created without interruption for removal of excised tissue all using the same apparatus.

Another advantage of the present invention includes providing a measurement device for setting the distance within the muscle tissue at which the tissue shall be excised.

Another optional advantage of the present invention includes providing an apparatus and method using a leading laser tip delivering low level thermal damage to reduce the force necessary for piercing of the epicardium and advancing the tool through or into the myocardium. The apparatus is thereby easier to control and manipulate by the surgeon, causes less bleeding at the epicardial surface than using a higher power laser and less fibrosis overall than using a mechanical piercing tool, and provides supplemental angiogenic stimulation by thermal damage of the myocardium.

An additional advantage of the invention is to provide an apparatus and method with a timing mechanism allowing the punching means to open and then rapidly close at the highest point of contraction at systole thereby allowing tissue to enter the gap created by the opening initially and then cutting the tissue within the gap which controls the size of tissue removed and reduces the arrhythmic side effects of removing the tissue. A further advantage is to have the timing mechanism directly reflect the contraction of the muscle by means of a pressure measurement.

A further advantage of the present invention is providing a method and apparatus for drug delivery to introduce substances with at least one pharmacologically active compound into the pockets and/or channels created. More particularly, an advantage of the invention includes providing a continuous flow drug delivery means and/or a pulsed drug delivery means where the pulsed drug delivery means introduces a bolus of substance timed and directed to release at the location and moment of pocket creation.

The present invention comprises a method and apparatus for creating pockets containing substances with pharmacologically active compounds within muscle tissue. One example of muscle tissue where the method and use of the apparatus is very applicable is ischemic myocardial tissue in need of high localized concentrations of angiogenic factors. Other examples include tumors and bone.

A mechanical excising device including a tapered dilator tip combined with an elongated flexible low-powered lasing apparatus at the dilator tip, such lasing apparatus including at least one optical fiber, is inserted via surgical incision and guided to the location exterior to the designated organ or body tissue to be treated. For example, with treating the myocardium of a ventricle of the heart, the device is inserted into the chest cavity of a patient and guided to an area exterior to the ventricle. The low-powered optical fiber lasing apparatus at the dilator tip of the device is activated and disperses low level thermal trauma upon contact thus reducing the force necessary to advance the dilator tip through the epicardium and myocardium to create a tunnel passage for the device. The thermal damage also reduces the overall bleeding in the myocardium and the tendency towards fibrosis with mechanical trauma, and increases the stimulation of angiogenesis in neighboring myocardial tissue.

The surgeon advances the excising tool to a designated distance by means of a hand-held control device. The excising tool is connected to the hand-held control device, and its attachment is secured by a trap slide means. A synchronized timing means (for example, an intramyocardial pressure detector or an EKG), optionally is synchronized with the hand-held control device to determine the opening and closing of the punching mechanism of the excising tool allowing myocardial tissue to enter the gap created by the opening and then be cut by rapid closure of the sharpened edges of the punch at maximum contraction at systole, thus creating a pocket within the tissue. The synchronized timing means preferably is a pressure detector located on the surface of the excising tool and connected with a power means for activating the punch mechanism. An insertion means within the device optionally introduces a substance, preferably containing a pharmacologically active compound, into the pocket to maintain a sufficient concentration of such a compound within the localized tissue. Such insertion means may be a continuous flow mechanism and/or be simultaneously triggered to deliver a bolus of the substance into the pocket with punch closure. For example, for intramyocardial pockets, an angiogenic compound such as VEGF may be inserted into the pockets to increase the angiogenesis within surrounding myocardial tissue. The device will then be moved within the myocardium to optionally create another intramyocardial pocket.

The advancement or withdrawal of the excising tool through the myocardium will be measured by a depth guide located on the surface of the excising tool. More particularly, the surgeon may optionally advance the excising tool through the myocardium and endocardium to the point of entry into the ventricle whereupon the surgeon will detect the significant reduction in pressure necessary to advance the tool. At this point, the surgeon may optionally withdraw the excising tool through the myocardium, creating pockets at designated depths along its path. Alternatively, the surgeon may optionally have already created pockets on the advancement of the excising tool through the myocardium, obviating the need to create pockets upon its withdrawal. The pockets are created by the Surgeon's trigger of a release button on the hand-held control device and coordinately also based on the synchronized timing mechanism.

The excised tissue is trapped within a reservoir means within the excising tool. With closure of the punching mechanism, the trapped tissue is compressed into the reservoir. Optionally, a means of measuring the filling of the reservoir is provided on the hand-held control device. Alternatively, after a set number of punches, for example five, the surgeon may manually empty the reservoir means or the excising tool may automatically require resetting mandating an emptying of the reservoir outside the body. The reservoir means may be emptied upon complete removal of the excising tool from the chest cavity, opening of the punching mechanism, forward expulsion of the tissue out of the opening by a plunger means within the excising tool and brushing off the extruding tissue. The foregoing methods of handling the excised tissue allows for the process of creating multiple pockets for drug delivery within each channel passage of the tool through the myocardium.

DETAILED DESCRIPTION OF EMBODIMENT

Figure 1:
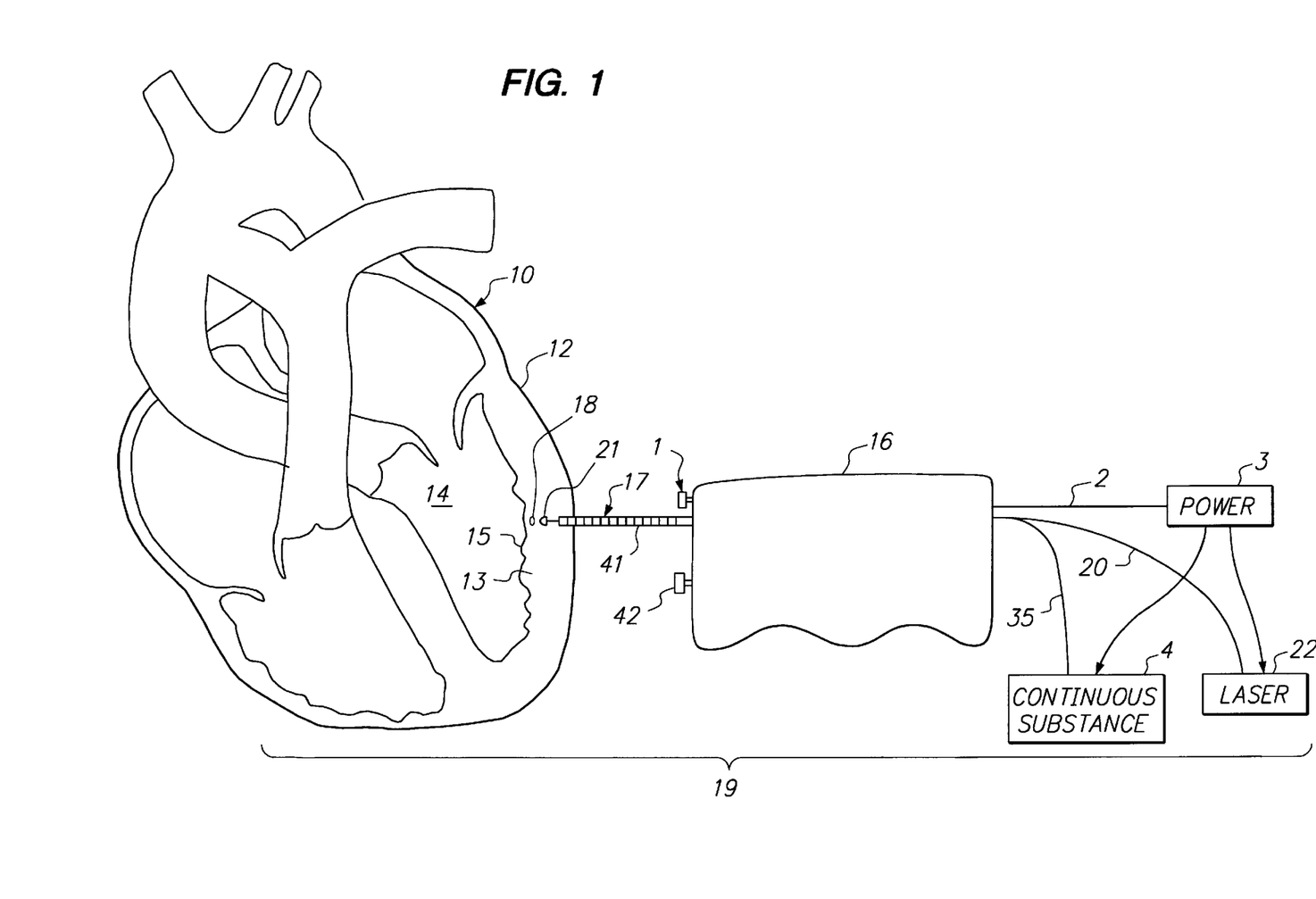
FIG. 1 is a diagrammatic view of a heart, partly in section, showing a device for creating a drug-filled pocket.

With reference to the drawing, FIG. 1 diagrammatically depicts a human heart with the epicardium 12 of the left ventricle 14 exposed where a stimulation/drug pocket formation procedure according to the invention is to be performed. Preliminary to the procedure, the surgeon makes an incision in the patient's chest to expose the outer wall (epicardium) of the heart's left ventricle. In a human heart, the wall of the left ventricle is comprised of an outer layer, the epicardium 12, the main muscle thickness, the myocardium 13, and the inner layer or endocardium 15. The epicardium is comprised of a smooth moist serous membrane which is somewhat tougher than the other tissue layers of the heart muscle.

Figure 4:
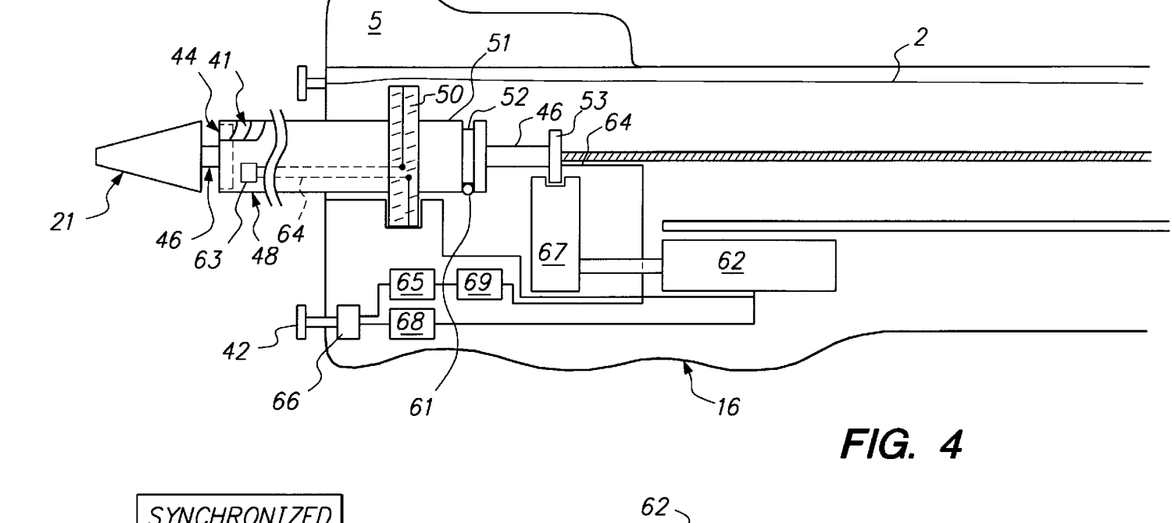
FIG. 4 is a partial longitudinal section view of the device of FIG. 1 showing the excising assembly as it is connected to a hand-held control device.
Figure 6A:
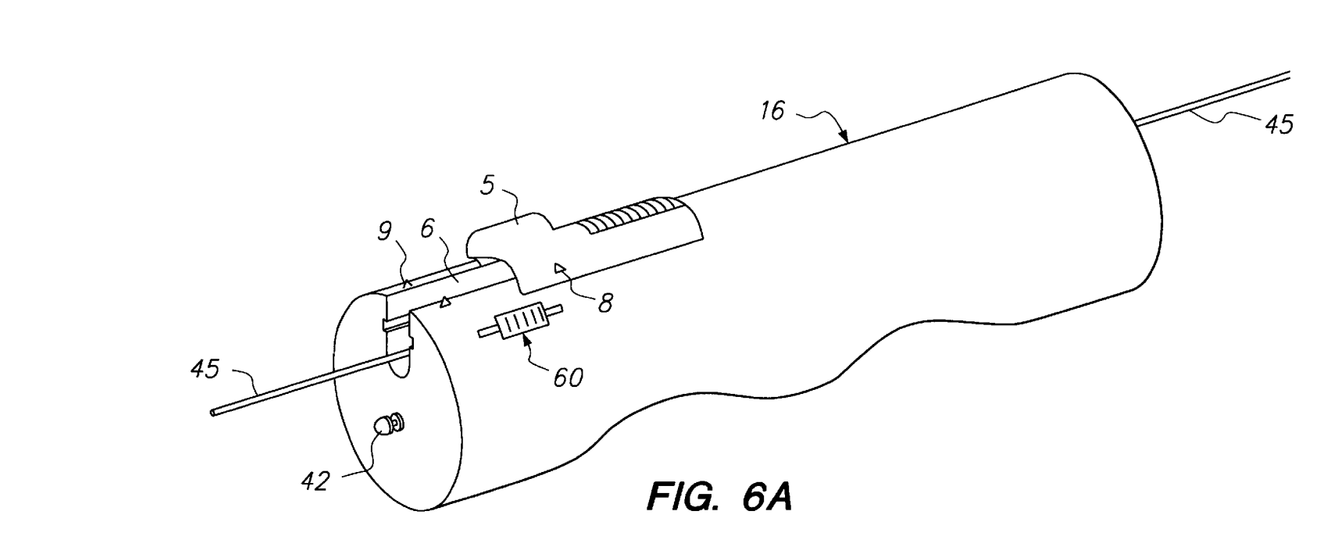
FIG. 6A is an outside view of the hand-held control device of FIG. 4 showing a locking trap slide in its open position and the combined fiber/insertion cable for inserting into the excising assembly.
Figure 6B:
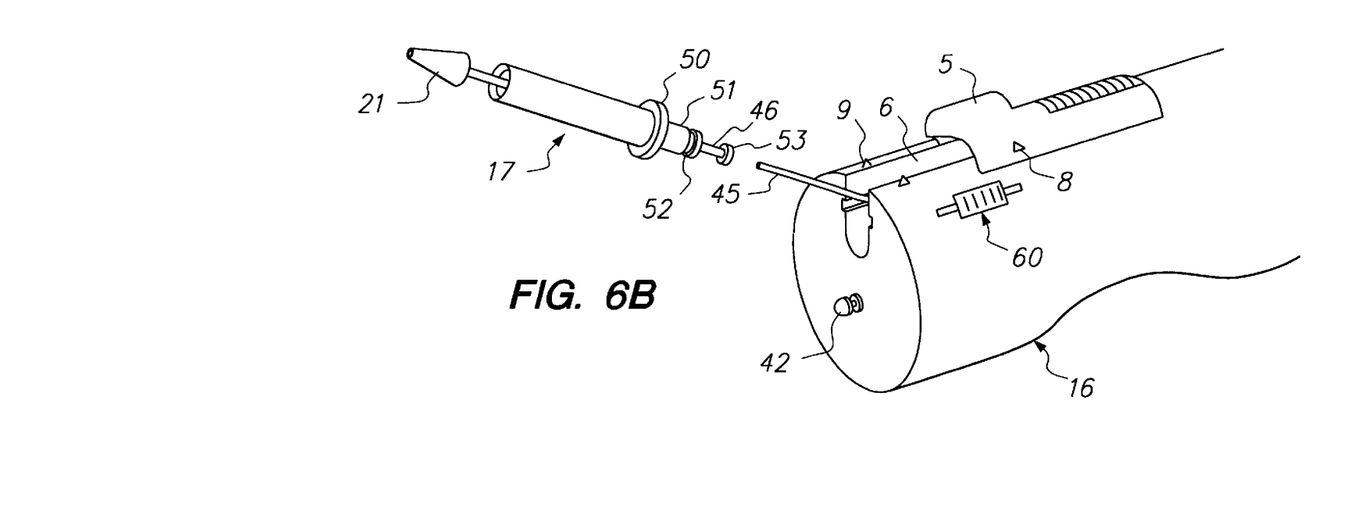
FIGS. 6B–6C demonstrates how the excising assembly of FIG. 2 is inserted into the hand-held control device of FIG. 4 and locked into place.
Figure 6C:
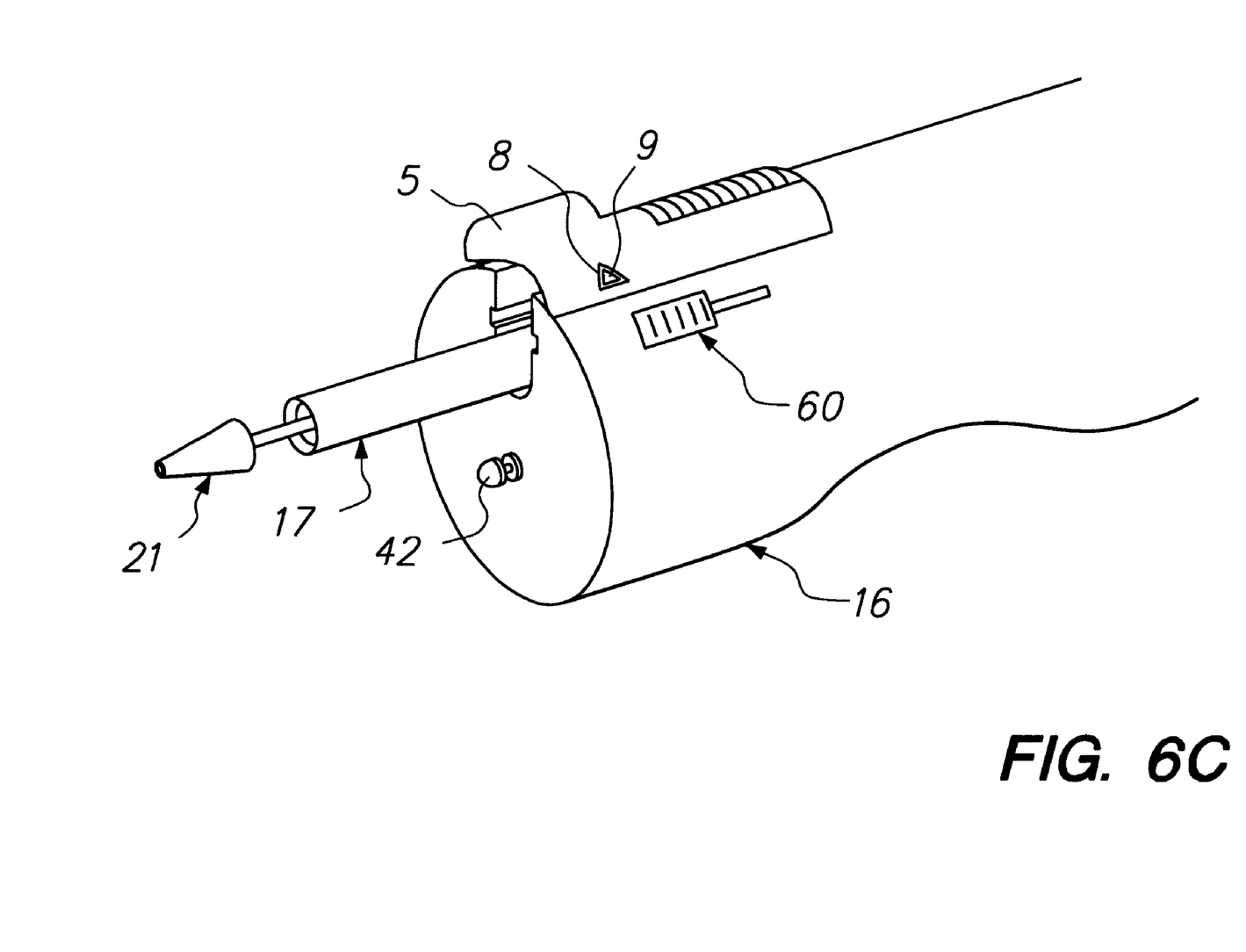

In accordance with the method of the present invention, the surgeon uses a hand-held control device 16 attached to an excising assembly 17 which is manipulated and operated to form a series of drug filled stimulation pockets 18 in the myocardium of the patient's heart at selected spaced apart locations. As will be described in greater detail below the apparatus 19 for creating pockets has an excising assembly 17 attached to a hand-held control device 16. As seen in FIG. 4, the proximal portion of the excising assembly 17 sits within the distal portion of the hand-held control device 16 and its placement is secured there by a locking slide trap 5. The locking slide trap 5, as seen in FIGS. 6A, 6B and 6C, slides along an opening 6 on the superior distal aspect of the hand-held control device 16. The locking slide trap 5 optionally may have one or more indentations 8 on its inferior surface that snap and connect with one or more protrusions 9 on the superior distal aspect of the hand-held control device 16. Once locked inside the hand-held control device 16, the excising assembly 17 optionally protrudes outward in a distal direction from a range of 3–5 cm.

Figure 3A:
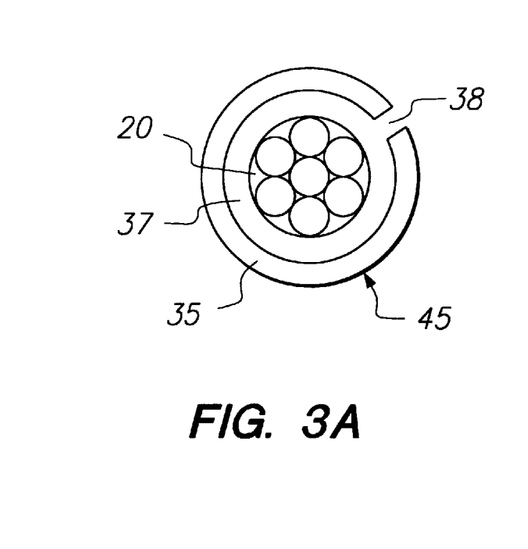
FIG. 3A is a view of the cross section of the distal end of the combined fiber/insertion cable.
Figure 3B:
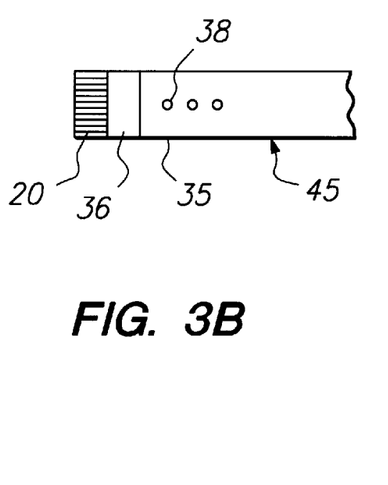
FIG. 3B is a view of the distal end of the combined optical fiber/insertion cable.
Figure 3C:
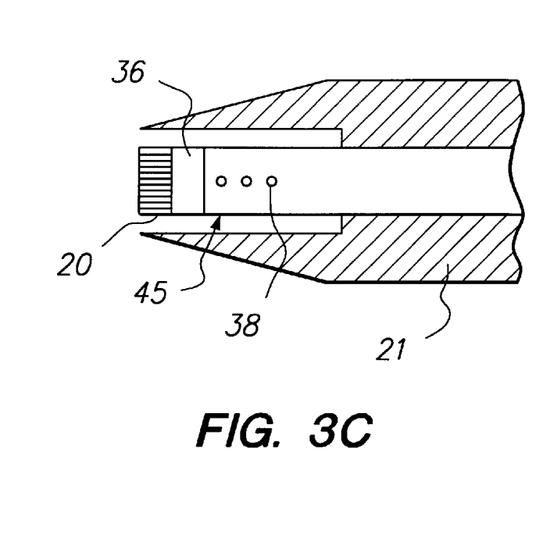
FIG. 3C is a view of the distal end of the tapered dilator tip including the combined optical fiber/insertion cable.

The excising assembly 17 has a tapered dilator tip 21 optionally having a distal end of an optical fiber means 20, preferably a bundle of fibers (see FIG. 1), which extends through the excising assembly 17 and the hand-held control device 16. The optical fiber means 20 may be of any design and may include single fibers as well as the preferred bundle of fibers. The tapered dilator tip 21 optionally has a length of about 1 to 2 mm. The excising assembly 17 also has a measurement scale 41 on its surface to indicate its depth of penetration within tissue. The proximal end of the optical fiber means 20 is connected to a source or generator 22 of laser energy which is preferably a Holmium laser that operates at a wave length in the range of 1.8–2.2 microns, a pulse frequency in the range of 2–25 Hertz and a power level range of approximately 0.6 J to 1.65 J, or an excimer laser may be used as well pressure from the source of the substance which location preferably is at the proximal end of the cylindrical shell insertion means 35. The substance is delivered to the tissues along the channels and pockets in the muscle created by the excising assembly through ports 38 in the cylindrical shell insertion means 35. The ports 38 are preferably located slightly proximal to the distal tip of the optical fiber means 20 and, if present, the annular tantalum marker 36, see FIGS. 3A, 3B and 3C.

Figure 7:
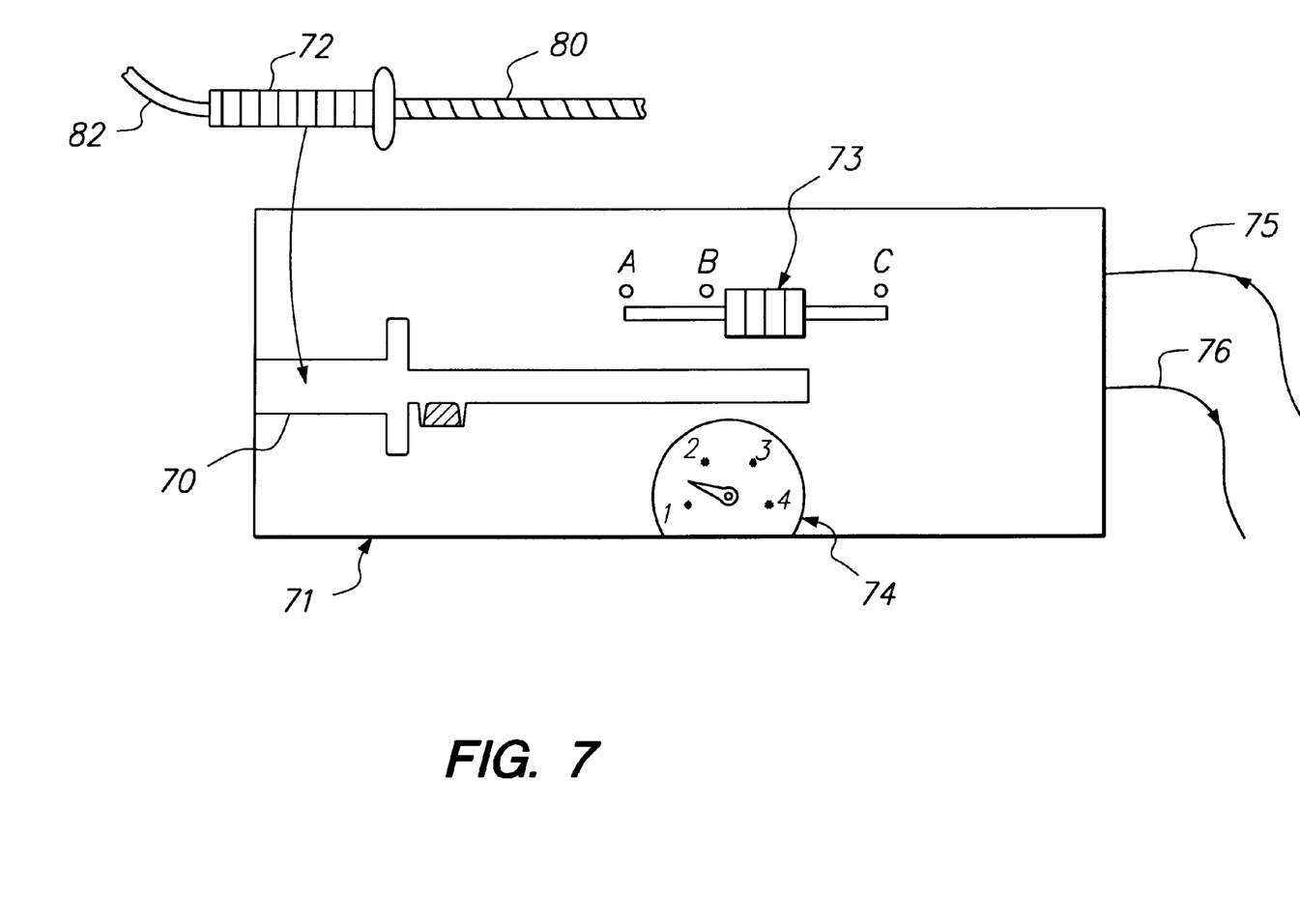
FIG. 7 is an outside view of the pump controller and syringe, the source and pumping unit for the substance that is delivered through the excising assembly.
Figure 8:
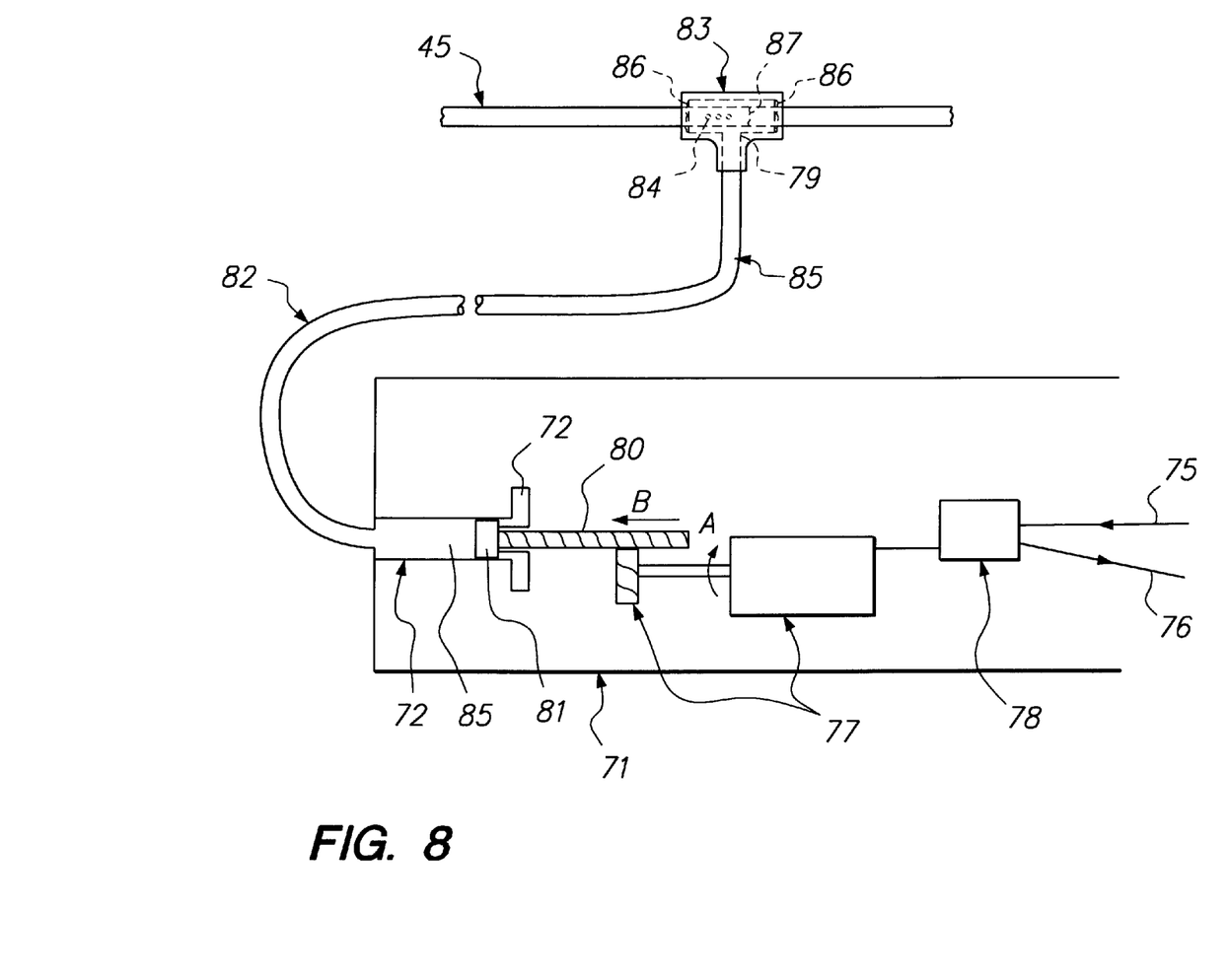
FIG. 8 demonstrates how the pump controller dispenses the substance for delivery into the combined fiber/insertion cable.

An optional source of the substance is a syringe 72 located in a pump controller 71 as seen in FIGS. 7 and 8. The syringe 72 fits within a syringe hold 70 within the pump controller 71. The plunger 81 of the syringe 72 could optionally have a screw 80 at its distal end which is turned moving the plunger 81 forward into the syringe 72 by a step motor 77 within the pump controller 71. For example, a black box 78 is connected to and powers the step motor 77 to rotate in direction A (as seen in FIG. 8) which causes the screw 80 to move in direction B. As the plunger 81 is moved distally within the syringe 72, the substance 85 within the syringe 72 is dispensed into a tubing 82 which ends in a T shaped junction 79. The combined optical fiber/insertion cable 45 runs within the top of the T shaped junction 79 of the tubing 82. The ends of the T shaped junction 79 are sealed around the combined optical fiber/insertion cable 45 by some sealing means, for example, glue at position 86. Inlet ports 84 of the cylindrical shell insertion means 35 of the combined optical fiber/insertion cable 45 allow for the inflow of the substance 85 from the tubing 82 within the T junction 79. The cylindrical shell insertion means 35 is sealed at a point 87 that is proximal to the inlet ports 84. The substance 85, therefore, moves in a distal direction within the cylindrical shell insertion means 35 towards the excising assembly 17. A sleeve 83 covers the T junction 79 to further support the integrity of the connection between the tubing 82 and the cylindrical shell insertion means 35 of the combined optical fiber/insertion cable 45.

The pump controller 71 has a drug delivery selection setting 74 on its surface to activate the pumping of the substance 85. As seen in FIG. 7, the drug delivery selection setting 74 could optionally provide settings for off (1), pump while lasing only (2), pump while punching pockets only (3) and pump while lasing and punching as other suitable medical lasers. This type of laser is preferable because it provides high absorption efficiency, hemostasis and a moderate absorption range in myocardium tissue, and is compatible with optical fiber delivery. The activated laser emitting a low-level energy laser beam through the distal end of the optical fiber means 20 provides a low energy ablation of tissue to ease the advancement of the dilator tip and excising assembly to pierce through the epicardium and tunnel through the myocardium. The laser is activated by depression of a foot switch which is connected to the power generator responsible for powering the laser source 22.

Figure 2:
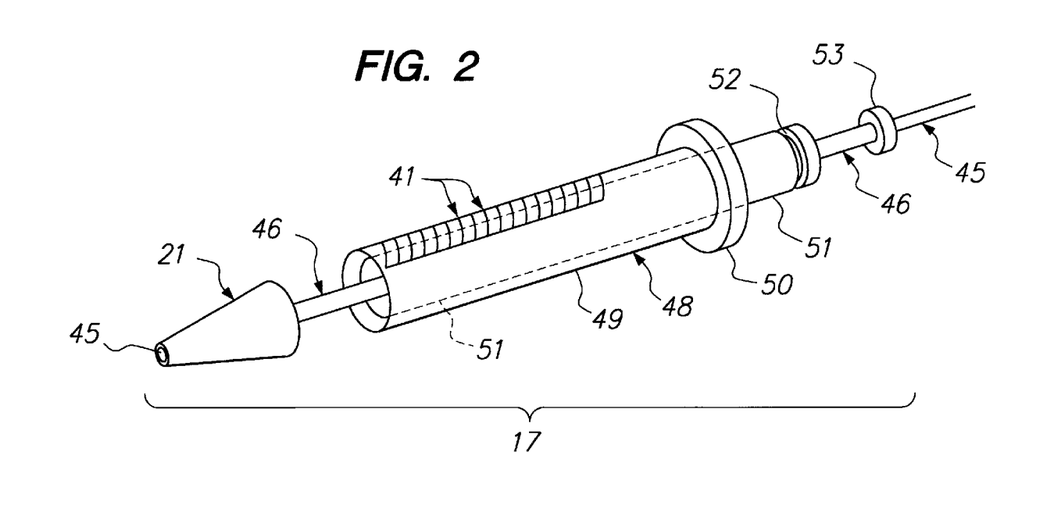
FIG. 2 is a view of an excising assembly portion of the device in FIG. 1 with its punching mechanism open as connected to a combined optical fiber/insertion cable.

At the laser generator, laser energy is supplied to the optical fiber means 20 which, at its distal end, as shown in FIG. 2, has a diameter of around 0.08–0.2 mm. The optical fiber means may be either a single fiber or comprised of a plurality (e.g. FIGS. 3A to 3C) of smaller glass fibers. The optical fiber means is optionally surrounded by a suitable plastic material 34, such as 353 ND Epoxy, which protects the glass fiber and is particularly useful in holding together multiple glass fibers. Near its distal tip, the bundle preferably is surrounded by an annular tantalum marker 36 which serves to retain the bundle closely packed in a proper geometric boundary. The layer surrounding the annular tantalum marker 36 and/or the plastic material 34 comprises a substance-filled cylindrical shell insertion means 35, preferably made of plastic such as polypropelene, having a wall thickness of 0.008 mm and equidistantly surrounding the optical fiber means 20 at a distance suitable to allow for delivery of drugs in the space (37) between the optical fiber means 20 and the shell 35. The optical fiber means 20 described is for purposes of illustration only and it will be recogized by those skilled in the art that single fibers and other laser delivery systems may be used. The optical fiber means 20 and the substance-filled cylindrical shell insertion means 35 as described above run together as the combined optical fiber/insertion cable 45.

The substance within the cylindrical shell insertion means 35 preferably comprises a fluid with at least one pharmacologically active compound or a flushing/cooling liquid such as a saline solution. The substance is propelled distally in the space 37 within the cylindrical shell insertion means 35 due to positive pockets (4). A speed setting 73 for the step motor 77 is also located on the surface of the pump controller 71. The speed setting 73 allows for 1) the stepping motors rate to be determined in cases of continuous flow of the substance, for example the step motor 77 turns at x steps per second, and 2) the number of steps to create a certain size drop of the substance 85, for example, large drops (5–20 steps) and small drops (1–3 steps). An incoming electrical wire 75 carries signal input to the black box indicating the timing of the laser and the punch of the excising assembly 17. An outgoing electrical wire 76 connects to a power source for powering the pump controller 71.

As seen in FIG. 2, the excising assembly 17 comprises two semi-dividable shell portions (distal 21 and proximal 48) unified by a common central rigid hollow cylinder 46 running the full length of the longitudinal axis of the excising assembly 17. The common central rigid hollow cylinder 46 extends beyond the span of the two shell portions (21 and 48) and ends proximally with the proximal end of a solenoid connector flange 53. The solenoid connector flange 53 comprises a relatively short cylindrical shell surrounding the common central rigid hollow cylinder 46 at the proximal end of the excising assembly 17. The common central rigid hollow cylinder 46 carries the combined optical fiber/insertion cable 45 within it from the distal through the proximal end of the excising assembly 17.

A tapered dilator tip 21, the distal semi-dividable shell portion of the excising assembly 17, has a proximal end comprising a closed surface lying flush against the common central rigid hollow cylinder 46 and has sharp edges along the perimeter of said proximal end. A reservoir/plunger portion 48, the proximal semi-dividable portion of the excising assembly 17, comprises two encircling cylindrical shell units (inner 51 and outer 49) further encircling the common central rigid hollow cylinder 46, and a control device flange 50.

The outer shell unit 49 comprises a rigid hollow cylinder of stainless steel having a diameter range of 0.5 to 2.0 mm having an open distal end with sharp edges and an open proximal end. A control device flange 50 comprising a rigid cylindrical shell is attached to the proximal end of the outer shell unit 49. The control device flange 50 connects in a removable manner the excising assembly 17 to the hand-held control device 16. The distal and proximal ends of the control device flange 50 preferably comprise closed surfaces to the point of their attachment with the outer shell unit 49 and the proximal end of the outer shell unit 49, respectively.

A cylindrical plunger 51, the inner cylindrical shell unit, has an outer cylindrical surface lying flush against the inner surface of the outer shell unit 49 and an inner cylindrical surface lying flush against the outer surface of the common central rigid hollow cylinder 46. Each surface of the cylindrical plunger 51 slides easily along the other surface it opposes. The distal and proximal ends of the cylindrical plunger 51 comprise closed surfaces. The distal end of the cylindrical plunger 51 preferably lies in its relaxed position somewhat proximally to the distal end of the outer shell unit 49. The proximal end of the cylindrical plunger 51 preferably protrudes in its relaxed position beyond the proximal end of the control device flange 50. Near its proximal end, the cylindrical plunger 51 has a slotted groove indentation 52 on its outer cylindrical surface. The cylindrical plunger 51 upon pressure applied to either of its ends can slide longitudinally within the outer shell unit 49 and along the common central rigid hollow cylinder 46. Upon pressure at its distal end, the cylindrical plunger 51 moves proximally within the outer shell unit 49 to create a reservoir means 44 for containing excised tissue. (See FIG. 2).

Upon a punch signal from the hand-held control device 16, the dilator tip portion 21 separates from the reservoir/plunger portion 48 to create a gap into which muscle tissue enters and then both semi-dividable portions close rapidly at their sharp edges. In this manner, the two semi-dividable portions of the excising assembly 17 operate as a punch to cut the muscle tissue. The punch signal is activated by a dual mechanism within the hand-held control device 16.

Figure 4A:
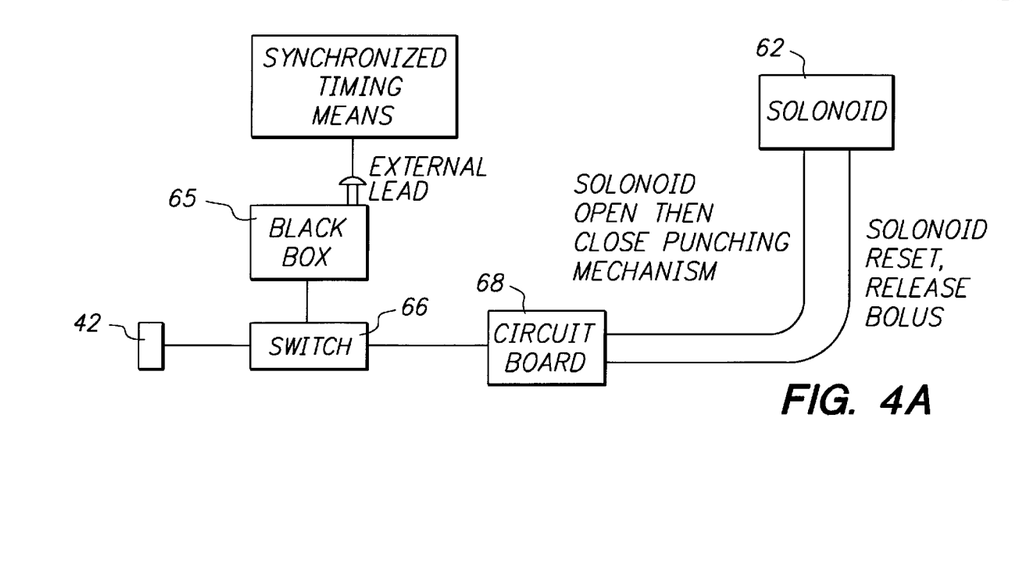
FIG. 4A is a diagram showing how a punching mechanism of the device in FIG. 4 is enabled by a synchronized timing means and an operator's switch.

As seen in FIGS. 4 and 4A, a black box 65 within the hand-held control device 16 preferably is connected to a synchronized timing means for sensing contractions and expansions of the beating heart. Preferably, the synchronized timing means comprises a pressure transducer 63, for example a thin film piezo electric pressure transducer, which optionally is located on the outer surface of the outer shell unit 49, and preferably the distal section of the outer shell unit 49, and electric wiring 64 connected to the pressure transducer distally. The electric wiring 64 runs proximally within the common central rigid hollow cylinder 46 into the hand-held control device 16 and to the black box 65. Optionally the synchronized timing means may be an EKG with signal input to the black box 65.

Figure 5:
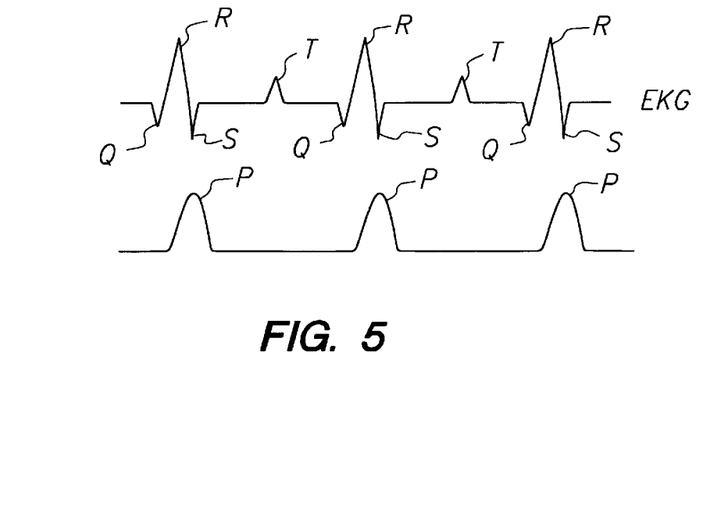
FIG. 5 demonstrates the corresponding wave patterns of an EKG and a pressure transducer.

Upon receiving the signal from the synchronized timing means, a comparison circuit within the black box 65 identifies the point of beginning systole (comparable to the peak of the R wave on an EKG, see FIG. 5). The solenoid powered forward may alternatively open or both open and close the punch mechanism by enabling a punch button switch 66 within the hand-held control device 16. In the first case, optionally the punch mechanism would open at beginning systole (e.g., maximum of R wave on the EKG) or at a threshold level of contractile pressure (e.g. maximum of P wave less 25%), and then close with the solenoid's reverse at a set time within the contraction, or preferably at the peak of contraction (S wave on the EKG or maximum of P wave on the pressure measurement). In the second case, the open/close action of the punch would occur sometime during systole, and preferably at a threshold of contractile pressure as discussed above. The punch button switch 66 must also be enabled from an operator's depression of a push button 42 on the surface of the hand-held control device 16. With the enablement from both the black box 65 and the push button switch 66, a signal is sent to a circuit board 68 which powers a solenoid 62 forward to operate the punch mechanism of the excising assembly 17 optionally opening it (as exampled above) at the point of beginning systole (peak of the R wave on an EKG) or at a minimum threshold of pressure and closing it at maximum contraction of systole (peak of the S wave on an EKG or the pressure wave peak, P, on a pressure transducer measurement scale, see FIG. 5). The source of electrical energy to the black box is from an adjacent battery 69.

The powered forward solenoid 62 propels a solenoid/flange connector 67 distally for approximately 1–3 mm within the hand-held control device 16 and then (or optionally with the solenoids reversal) pulls it back proximally in a rapid movement. The distal movement of the solenoid/flange connector 67 is optionally synchronized to occur at the point of beginning systole or at a minimum threshold of pressure and the proximal movement at the point of maximum contraction of systole. The solenoid/flange connector 67 has a slotted groove on its surface for holding part of the solenoid connector flange 53 of the excising assembly 17. The distal movement of the solenoid/flange connector 67 therefore also distally propels the common central rigid hollow cylinder 46 and its attached dilator tip portion 21, thereby opening a gap between the two semi-dividable portions (21 and 48) of the excising assembly 17 the same distance allowing myocardial tissue to enter the gap. At a certain point during systole, for example, maximum contraction of systole, the dilator tip portion 21 is rapidly pulled back to close upon the reservoir/plunger portion 48 thereby operating the punching mechanism to excise myocardial tissue and trap the tissue within the reservoir means 44.

The tissue trapped in the reservoir means 44 pushes up against the distal end of the cylindrical plunger 51, thereby sliding the cylindrical plunger 51 and its slotted groove indentation 52 in a proximal direction. As seen in FIGS. 4 and 6A, an excised tissue ejection indicator 60 on the hand-held control device 16 has a cross piece 61 that aligns with the inferior aspect of the slotted groove indentation 52. As the slotted groove indentation 52 moves proximally, so does the cross piece 61 thereby showing on the excised tissue selection indicator 60, the amount of excised tissue trapped within the reservoir means 44. Removal of the excising assembly 17 from the hand-held control device unit, allows for greater ease in forcing the cylindrical plunger 51 distally through the reservoir means 44 to release the trapped excised tissue.

Upon the operator's release of the push button switch 67, the solenoid 62 is reversed to allow it to be powered with the next doubly-enabled signal. Optionally, upon the solenoid's 62 reverse, the pump controller 71 is activated to send a bolus of pharmacologically active substance 85 through the tubing 82 and the cylindrical shell insertion means 35 to its distal open end at the tip of the dilator tip portion 21 which is positioned within the created pocket cavity upon its creation.

A surgeon by activating a laser switch, preferably a foot switch, activates laser emission through the optical fiber means 20 and depending on the position chosen on the drug delivery selection setting 74, the continuous flow of the pharmacologically active substance through the cylindrical shell insertion means 35. The surgeon then advances the excising assembly 17 through the epicardium 12 and into the myocardium 13. The surgeon passes the excising assembly 17 through the passage created, firing a punch button 42 on the hand-held control device 16 which thereby activates the punching mechanism within the excising assembly 17 to cut and store an excised piece of tissue and create an intramyocardial pocket. Preferably a substance is released through the portal of the cylindrical shell insertion means 35 at the distal end of the dilator tip portion 21 of the excising assembly 17 on a continuous-flow and/or bolus flow basis where the bolus of more preferably a pharmacologically active substance, for example VEGF, is released into the newly created pocket. A drug-filled pocket is thereby produced.

Preferably, the surgeon first passes the excising assembly 17 through the epicardium 12, myocardium 13 and endocardium 15 to enter the ventricle 14 whereupon the reduction in resistance met with further advancement of the excising assembly indicates to the surgeon the depth of the endocardium and the thickness of the heart wall relative to the measurement scale 41 on the surface of the excising assembly 17. The surgeon may alternatively withdraw the excising assembly 17 through the passage created firing the punch button 42 at designated distances within the wall of the myocardium 13 as measured on the measurement scale 41 during the withdrawal. The surgeon thereby creates drug filled pockets at designated depths within the myocardium.

Upon full retraction of the excising assembly 17 from the ventricle wall, the surgeon will continue with subsequent entries into the myocardium until the punch (the two semi-dividable portions of the excising assembly 17) dulls or the excised tissue ejection indicator 60 indicate the reservoir means 44 is full. At that point a change of excising assembly 17 for cleanout or sharpness will be done.

FIGS. 6A through 6C, demonstrate how the excising assembly 16 is connected in a removable manner to the hand-held control device (16). The combined optical/insertion cable 45 is threaded from the hand-held control device (16) into the proximal end of the common central rigid hollow cylinder 46 of the excising assembly 17. Optionally the electrical wire 64 for the pressure transducer 63, runs along the outer surface of the outer shell unit 49 to connect to 360 degree contact strips on the surface of the control device flange 50, which upon contact with the housing in the hand-held control device 16, conducts signals to the black box 65 within the hand-held control device. The excising assembly 16 is then inserted into the hand-held control device 16 while the trap slide 5 of the hand-held control device 16 is in its open position. Once the excising assembly 17 is in its proper position within the hand-held control device 16, then the trap slide 5 is pushed distally to lock it closed by snapping the indentations 8 on the locking trap slide 5 into the protrusions 9 on the hand-held control device 16, and thereby securing the excising assembly 17.

As will be understood by those familiar with the art, the present invention may be embodied in other specific forms without departing from the spirit or essential characteristics thereof. The scope of the present invention is therefore limited only by the scope of the claims appended hereto.

I claim:

1. A method for revascularizing tissue by facilitating intracapillary connections therein comprising the acts of:

a) providing a mechanical excising apparatus having proximal and distal ends and a tissue entrapping mechanism, the distal end having a tapered dilator tip, the proximal end having a controller operably connected to the tissue entrapping mechanism;

b) placing by surgical incision the distal end of the excising apparatus at a surface of target tissue to be revascularized;

c) advancing the distal end of the excising apparatus within the target tissue by causing the dilator tip to tunnel into the target tissue;

d) operating the controller to open the tissue entrapping mechanism enabling a portion of the target tissue to bulge into the open tissue entrapping mechanism, the controller further causing the tissue entrapping mechanism to close and cut the bulged portion from the target tissue, the cut tissue trapped within the excising apparatus; and e) withdrawing the excising device.

2. The method of claim 1 wherein act b) comprises placing the distal end of the excising tool at an epicardial surface of a heart; act c) comprises advancing to a designated distance within myocardium; and act d) comprises cutting at least one portion from the myocardium.

3. The method of claim 2 wherein act d) is performed at least during act e) while withdrawing the excising tool.

4. The method of claim 2 wherein act d) is performed at least during act c) while advancing within the myocardium.

5. The method of claim 2 wherein in act d) the cutting causes creating of a pocket in the myocardium.

6. The method of claim 2 further comprising the act of setting a designated advancement distance prior to act c) of advancing the distal end of the excising tool.

7. The method of claim 2 wherein act d) further comprises synchronizing the opening and closing to occur within a systolic period of a heart cycle.

8. The method of claim 2 comprising the act of delivering a drug to the myocardium at least during step d).

9. The method of claim 2 further comprising prior to act c) the act of delivering energy from an energy delivery device to ease advancement of the excising apparatus.

10. A method for revascularizing tissue by facilitating intracapillary connections therein comprising the acts of:

a) providing a mechanical excising tool having proximal and distal ends and a tissue gap mechanism, the distal end having a tapered dilator tip, the proximal end having a hand-held controller;

b) placing by surgical incision the distal end of the excising tool at a surface of target tissue to be revascularized;

c) advancing the distal end of the excising tool within the target tissue by exerting force on the dilator tip to tunnel into the target tissue;

d) operating the controller to open the tissue gap mechanism enabling a portion of the target tissue to enter into the tissue gap mechanism, the controller further causing the tissue gap mechanism to close and cut the portion from the target tissue, the cut tissue trapped within the excising tool, the cutting causing an injury in the target tissue which facilitates intracapillary connections; and e) withdrawing the excising tool.

11. The method of claim 10 wherein act d) is performed at least during act e) while withdrawing the excising tool.

12. The method of claim 10 wherein act d) is performed at least during act c) while advancing within the target tissue.

13. The method of claim 10 wherein in act d) the cutting causes creation of a pocket in the target tissue.

14. The method of claim 10 further comprising the act of setting a designated advancement distance prior to act c) of advancing of the distal end of the excising tool.

15. The method of claim 10 wherein act d) further comprises synchronizing the opening and closing to occur within a systolic period of a heart cycle.

16. The method of claim 10 comprising the act of delivering to the target tissue a drug at least during step d).

17. The method of claim 10 wherein act b) comprises placing the distal end of the excising tool at an epicardial surface of a heart; act c) comprises advancing to a designated distance within myocardium; and act d) comprises cutting a portion from the myocardium.

18. A method for revascularizing tissue by facilitating intracapillary connections therein comprising the acts of:

a) providing a mechanical excising device having proximal and distal ends, a tissue gap mechanism, and a energy delivery device extending into the distal end, the distal end having a tapered dilator tip, the proximal end having a controller operably connected to the tissue gap mechanism;

b) placing by surgical incision the distal end of the excising device at the surface of target tissue to be revascularized;

c) delivering energy through the energy delivery device to the target tissue to ease advancement of the excising device through the target tissue;

d) advancing the distal end of the excising device within the target tissue;

e) operating the controller to open the tissue gap mechanism enabling tissue to enter therein, the controller further causing the tissue gap mechanism to close and to cut the entered tissue from the target tissue; and f) withdrawing the excising device and the cut tissue thereby causing an injury which facilitates intracapillary connections.

19. The method of claim 18 wherein act c) comprises delivering laser energy to pierce through epicardium.

20. The method of claim 18 wherein act e) is performed at least during act f) while withdrawing the excising tool.

21. The method of claim 18 wherein act e) is performed at least during act d) while advancing within the target tissue.

22. The method of claim 18 wherein in act e) the cutting causes creation of a pocket in the target tissue.

23. The method of claim 18 further comprising the act of setting a designated advancement distance prior to act c) of advancing of the distal end of the excising tool.

24. The method of claim 18 wherein act e) further comprises synchronizing the opening and closing to occur within a systolic period of a heart cycle.

25. The method of claim 18 wherein act b) comprises placing the distal end of the excising tool at an epicardial surface of a heart; act c) comprises delivering laser energy to ease advancement of the excising device; act d) comprises advancing the excising device within myocardium; and act e) comprises cutting a portion from the myocardium.

26. The method of claim 18 comprising the act of delivering to the target tissue a drug at least during step e).

27. The method of claim 26 wherein delivering the drug occurs continuously during acts d) and e).

28. The method of claim 26 wherein delivering the drug occurs continuously during act e).

29. The method of claim 26 wherein delivering the drug occurs following act e).

30. The method of claim 26 wherein delivering the drug further comprises delivering at least one bolus of drug during acts d) and e).

31. The method of claim 26 wherein delivering the drug further comprises delivering at least one bolus of drug during act e).

32. The method of claim 26 wherein delivering the drug further comprises delivering at least one bolus of drug following act e).

33. The method of claim 26 wherein delivering the drug further comprises selecting a flow rate for delivering the drug.

34. A method for revascularizing tissue by facilitating intracapillary connections therein comprising the acts of:
  a) providing a mechanical excising device having proximal and distal ends, a conduit within at least the distal end, and a tissue gap mechanism, the distal end having a tapered dilator tip, the proximal end having a drug source connected to the conduit and a controller operably connected to the tissue gap mechanism;
  b) placing by surgical incision the distal end of the excising device at a surface of target tissue to be revascularized;
  c) advancing the distal end of the excising device within the target tissue by tunneling with the dilator tip;
  d) operating the controller to open the tissue gap mechanism enabling a portion of the target tissue to enter into the tissue gap mechanism, the controller further causing the tissue gap mechanism to close and cut the portion from the target tissue, the cut portion trapped within the excising device;
  e) delivering a drug from the drug source through the conduit to facilitate angiogenesis; and
  f) withdrawing the excising device and the cut portion.

35. The method of claim 34 wherein act e) occurs continuously during acts c) and d).

36. The method of claim 34 wherein act e) occurs continuously during act d).

37. The method of claim 34 wherein act e) occurs following act d).

38. The method of claim 34 wherein act e) further comprises delivering at least one bolus of drug during acts c) and d).

39. The method of claim 34 wherein act e) further comprises delivering at least one bolus of drug during act d).

40. The method of claim 34 wherein act e) further comprises delivering at least one bolus of drug after act d).

41. The method of claim 34 wherein act e) further comprises selecting a flow rate for delivering the drug.

42. The method of claim 34 further comprising the act of using the controller to activate performance of act e).

43. The method of claim 34 wherein the cutting in act d) creates a pocket within myocardium and the drug is delivered into the pocket in act e).

44. The method of claim 43 wherein act e) comprises depositing a bolus of VEGF into the pocket.

* * * * *